(12) United States Patent
De La Cruz et al.

(10) Patent No.: US 8,697,682 B2
(45) Date of Patent: *Apr. 15, 2014

(54) SALTS

(71) Applicants: Marilyn De La Cruz, Matawan, NJ (US); Piotr H. Karpinski, Lincoln Park, NJ (US); Yugang Liu, Bridgewater, NJ (US)

(72) Inventors: Marilyn De La Cruz, Matawan, NJ (US); Piotr H. Karpinski, Lincoln Park, NJ (US); Yugang Liu, Bridgewater, NJ (US)

(73) Assignee: Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/856,371

(22) Filed: Apr. 3, 2013

(65) Prior Publication Data

US 2013/0225550 A1 Aug. 29, 2013

Related U.S. Application Data

(62) Division of application No. 13/140,490, filed as application No. PCT/US2009/068352 on Dec. 17, 2009, now Pat. No. 8,486,930.

(60) Provisional application No. 61/203,051, filed on Dec. 18, 2008.

(51) Int. Cl.
*A61K 31/397* (2006.01)
*C07D 205/04* (2006.01)

(52) U.S. Cl.
CPC ................................. *A61K 31/397* (2013.01); *C07D 205/04* (2013.01)
USPC ..................................... 514/210.17; 548/953

(58) Field of Classification Search
None
See application file for complete search history.

(56) References Cited

FOREIGN PATENT DOCUMENTS

| WO | 2004/103306 A2 | 12/2004 |
|---|---|---|
| WO | WO 2004103306 A2 * | 12/2004 |
| WO | 2006/058316 A1 | 6/2006 |
| WO | 2007/021666 A2 | 2/2007 |
| WO | 2008/000419 A1 | 1/2008 |

OTHER PUBLICATIONS

Hörig et al., J. Translational Med. 2:44 (2004).*
Stahl, P. Heinrich et.al.,; The Practice of Medicinal Chemistry, Academic Press, London XP002566271 pp. 601-615; (2003).
Caira M R, et.al.,; Topics in Current Chemistry, vol. 198; Springer Verla, Berlin, pp. 163-208 ; XP001156954; (1998).
Berge Stephen, Journal of Pharmaceutical Sciences vol. 66 No. 1, pp. 1-19 (1977).

* cited by examiner

*Primary Examiner* — Michael Barker
(74) *Attorney, Agent, or Firm* — Jim Lynch (57) ABSTRACT

This invention relates to a hydrochloride, malate, oxalate and tartrate salt forms of 1-(4-{1-[(E)-4-cyclohexyl-3-trifluoromethyl-benzyloxyimino]-ethyl}-2-ethyl-benzyl)-azetidine-3-carboxylic acid (Compound I), to pharmaceutical compositions comprising this salt, to processes for forming this salt and to its use in medical treatment. In addition, the present invention also relates to new polymorphic forms of each of these salts, as well as to pharmaceutical compositions comprising these polymorphic forms, to processes for obtaining them, and their use in medical treatment.

20 Claims, 3 Drawing Sheets

SALTS

FIELD OF THE INVENTION

This invention relates to novel salt forms of 1-(4-{1-[(E)-4-cyclohexyl-3-trifluoromethyl-benzyloxyimino]-ethyl}-2-ethyl-benzyl)-azetidine-3-carboxylic acid (hereinafter referred to as Compound I), to pharmaceutical compositions comprising these salt forms, to processes for forming them, and to their use in medical treatment. In addition, the present invention also relates to particular polymorphic forms of the novel salt forms of Compound I, as well as to pharmaceutical compositions comprising these polymorphic forms, to processes for obtaining them, and their use in medical treatment.

BACKGROUND OF THE INVENTION

It is important to identify forms of a drug that can be conveniently manufactured, formulated and administered to a patient.

Furthermore, in the manufacture of oral drug compositions, it is important that the drug is in a form that provides reliable and reproducible plasma concentrations following administration to a patient.

Chemical stability, solid state stability and "shelf life" of the drug substance are also a particularly important factors. The drug substance, and compositions containing it, should ideally be capable of being effectively stored over appreciable periods of time, without exhibiting a significant change in the active component's physico-chemical characteristics (e.g. its chemical composition, density, hygroscopicity and solubility).

Moreover, it is also important to be able to provide drug in a form which is as chemically pure as possible.

It is known that amorphous drug materials may present some problems in this regard. For example, such materials are typically difficult to handle and to formulate, provide for unreliable solubility, and are often found to be unstable and chemically impure.

The skilled person will therefore appreciate that, if a drug can be readily obtained in a stable crystalline form, many of the above problems may be solved. Thus, in the manufacture of commercially viable, and pharmaceutically acceptable, drug compositions, it is important, wherever possible, to provide drug in a substantially crystalline and stable form. It is to be noted, however, that this goal is not always achievable. Indeed, based on molecular structure alone, it is not typically possible to predict what the crystallisation behaviour of a compound, either as such or in the form of a salt, will be. This can only be determined empirically.

WO2004/103306, the entire contents of which are incorporated herein by reference, discloses a series of compounds capable of inhibiting EDG receptors. WO2004/103306 teaches that the compounds disclosed therein are potentially useful agents for use in the therapy of a number of medical conditions mediated by lymphocytes, such as, for example, transplant rejection, autoimmune conditions and cancer. A full list of possible conditions is recited at page 13, line 9 to page 14, line 3 of WO2004/103306. One particular compound disclosed in WO2004/103306 is 1-(4-{1-[(E)-4-cyclohexyl-3-trifluoromethyl-benzyloxyimino]-ethyl}-2-ethyl-benzyl)-azetidine-3-carboxylic acid (Compound I), the structure of which is shown below.

Compound I

However, there is no disclosure in WO2004/103306 of any salt or crystalline forms of Compound I.

DISCLOSURE OF THE INVENTION

We have found that the certain crystalline salt forms of Compound I possess advantageous pharmaceutical properties.

The Hydrochloride Salt of Compound I

We have now found that Compound I can be obtained as a hydrochloride salt, which possesses a number of advantageous pharmaceutical properties (including, for example, favourable stability and low hygroscopicity).

Therefore, in a first aspect, the present invention provides a hydrochloride salt of Compound I.

The hydrochloride salt of Compound I may exist in a crystalline form.

Suitably, the hydrochloride salt of Compound I is substantially crystalline. By "substantially crystalline", we mean that the degree of crystallinity, as determined by X-ray powder diffraction data, is conveniently greater than about 20%, more conveniently greater than 60%, even more conveniently greater than about 80%, and preferably greater than about 90%.

According to a further aspect, the present invention provides Crystalline Form A of the hydrochloride salt of compound I.

Figure 1:
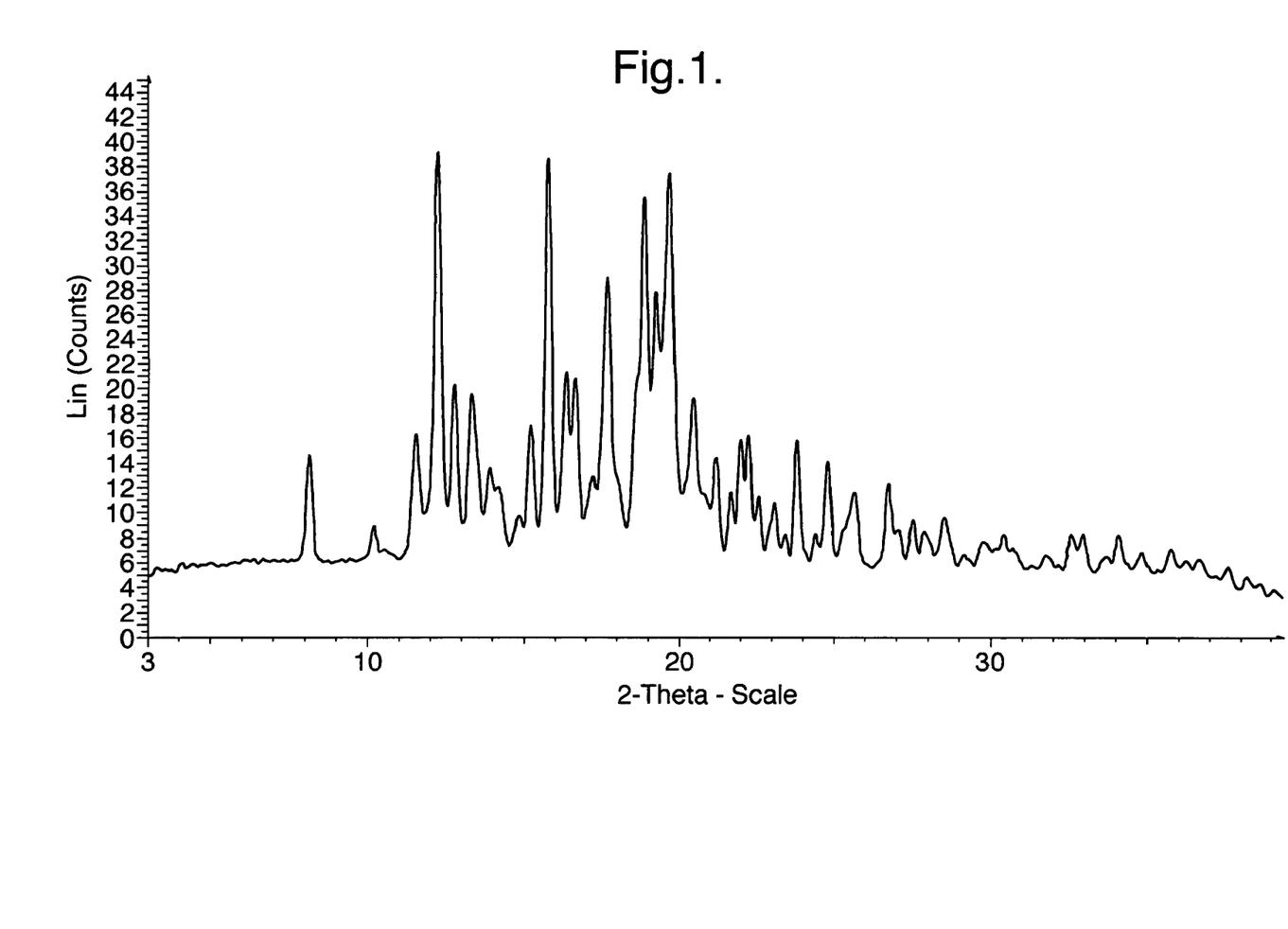
FIG. 1 shows the XRPD-diffractogram of Crystalline Form A of the HCl salt of Compound I.

The Crystalline Form A of the hydrochloride salt of Compound I is characterised in that it provides an X-ray powder diffraction pattern substantially as shown in FIG. 1.

The most prominent X-ray powder diffraction peaks for the Crystalline Form A of the hydrochloride salt of Compound I are shown in Table 1:

TABLE 1

The most prominent peaks of Crystalline Form A of the hydrochloride salt of Compound I

| 2-Theta in deg | d value in Angstrom | Intensity* |
|---|---|---|
| 8.1 | 10.870 | Medium |
| 10.2 | 8.668 | Medium |
| 11.5 | 7.679 | Medium |
| 12.2 | 7.232 | Strong |
| 12.8 | 6.934 | Medium |
| 13.3 | 6.642 | Medium |
| 13.9 | 6.356 | Medium |
| 14.3 | 6.206 | Medium |
| 15.2 | 5.807 | Medium |
| 15.8 | 5.601 | Strong |
| 16.4 | 5.409 | Medium |
| 16.6 | 5.324 | Medium |
| 17.7 | 5.020 | Medium |
| 18.9 | 4.683 | Strong |
| 19.3 | 4.602 | Medium |
| 19.7 | 4.497 | Strong |
| 20.5 | 4.334 | Medium |

TABLE 1-continued

The most prominent peaks of Crystalline Form
A of the hydrochloride salt of Compound I

| 2-Theta in deg | d value in Angstrom | Intensity* |
|---|---|---|
| 21.2 | 4.182 | Medium |
| 22.0 | 4.033 | Medium |
| 22.3 | 3.980 | Medium |
| 23.8 | 3.731 | Medium |

*peak intensities were assigned as follows: Small = 1% to 19.9% the intensity of the most intense peak; Medium = 20% to 79.9% the intensity of the most intense peak; and Strong = 80% or above of the intensity of the most intense peak According to the present invention there is provided Crystalline Form A of the hydrochloride salt of Compound I, wherein said Crystalline Form has an X-ray powder diffraction pattern with at least one specific peak at about 2-theta=12.2°, 15.8°, 18.9°, or 19.7°.

According to the present invention there is provided Crystalline Form A of the hydrochloride salt of Compound I, wherein said Crystalline Form has an X-ray powder diffraction pattern with specific peaks at about 2-theta=12.2°, 15.8°, 18.9°, and 19.7°.

According to the present invention there is provided Crystalline Form A of the hydrochloride salt of Compound I, wherein said Crystalline Form has an X-ray powder diffraction pattern with at least one specific peak at about 2-theta=8.1°, 12.2°, 15.8°, 18.9°, or 19.7°.

According to the present invention there is provided Crystalline Form A of the hydrochloride salt of Compound I, wherein said Crystalline Form has an X-ray powder diffraction pattern with specific peaks at about 2-theta=8.1°, 12.2°, 15.8°, 18.9°, and 19.7°.

According to the present invention there is provided Crystalline Form A of the hydrochloride salt of Compound I, wherein said Crystalline Form has an X-ray powder diffraction pattern with specific peaks at about the values listed in Table 1 above.

According to the present invention there is provided Crystalline Form A of the hydrochloride salt of Compound I, wherein said Crystalline Form has an X-ray powder diffraction pattern substantially the same as the X-ray powder diffraction pattern shown in FIG. 1.

The Malate Salt of Compound I

We have also found that Compound I can be obtained as a malate salt, which also possesses a number of advantageous pharmaceutical properties.

Therefore, in a further aspect, the present invention provides a malate salt of Compound I.

The malate salt of Compound I may exist in a crystalline form.

Suitably, the malate salt of Compound I is substantially crystalline.

According to a further aspect, the present invention provides Crystalline Form A of the malate salt of compound I.

Figure 2:
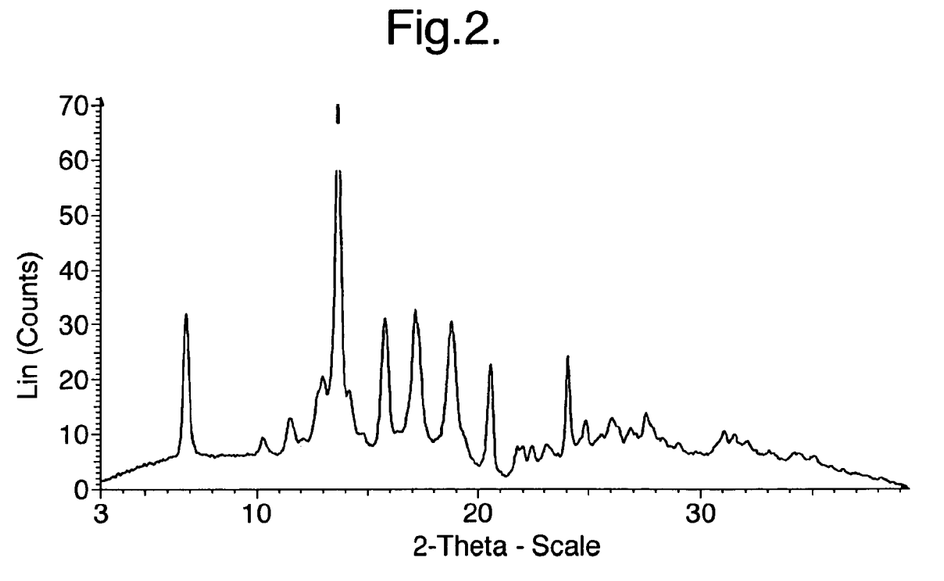
FIG. 2 shows the XRPD-diffractogram of Crystalline Form A of the malate salt of Compound I.

The Crystalline Form A of the malate salt of Compound I is characterised in that it provides an X-ray powder diffraction pattern substantially as shown in FIG. 2.

The most prominent X-ray powder diffraction peaks for the Crystalline Form A of the malate salt of Compound I are shown in Table 2:

TABLE 2

The most prominent peaks of Crystalline
Form A of the malate salt of Compound I

| 2-Theta in deg | d value in Angstrom | Intensity |
|---|---|---|
| 6.8 | 12.968 | Medium |
| 10.2 | 8.668 | Small |
| 11.5 | 7.704 | Small |
| 13.7 | 6.478 | Strong |
| 15.8 | 5.616 | Medium |
| 17.2 | 5.164 | Medium |
| 18.8 | 4.713 | Medium |
| 20.5 | 4.320 | Medium |
| 24.1 | 3.693 | Medium |

* peak intensities were assigned as follows: Small = 1% to 19.9% the intensity of the most intense peak; Medium = 20% to 79.9% the intensity of the most intense peak; and Strong = 80% or above of the intensity of the most intense peak According to the present invention there is provided Crystalline Form A of the malate salt of Compound I, wherein said Crystalline Form has an X-ray powder diffraction pattern with a specific peak at about 2-theta=13.7°.

According to the present invention there is provided Crystalline Form A of the malate salt of Compound I, wherein said Crystalline Form has an X-ray powder diffraction pattern with at least one specific peak at about 2-theta=6.8°, 13.7°, 15.8°, 17.2° or 20.5°.

According to the present invention there is provided Crystalline Form A of the malate salt of Compound I, wherein said Crystalline Form has an X-ray powder diffraction pattern with specific peaks at about 2-theta=6.8°, 13.7°, 15.8°, 17.2° and 20.5°.

According to the present invention there is provided Crystalline Form A of the malate salt of Compound I, wherein said Crystalline Form has an X-ray powder diffraction pattern with specific peaks at about the values listed in Table 2 above.

According to the present invention there is provided Crystalline Form A of the malate salt of Compound I, wherein said Crystalline Form has an X-ray powder diffraction pattern substantially the same as the X-ray powder diffraction pattern shown in FIG. 2.

The Oxalate Salt of Compound I

We have also found that Compound I can be obtained as an oxalate salt, which also possesses a number of advantageous pharmaceutical properties.

Therefore, in a first aspect, the present invention provides an oxalate salt of Compound I.

The oxalate salt of Compound I may exist in a crystalline form.

Suitably, the oxalate salt of Compound I is substantially crystalline.

According to a further aspect, the present invention provides Crystalline Form A of the oxalate salt of compound I.

Figure 3:
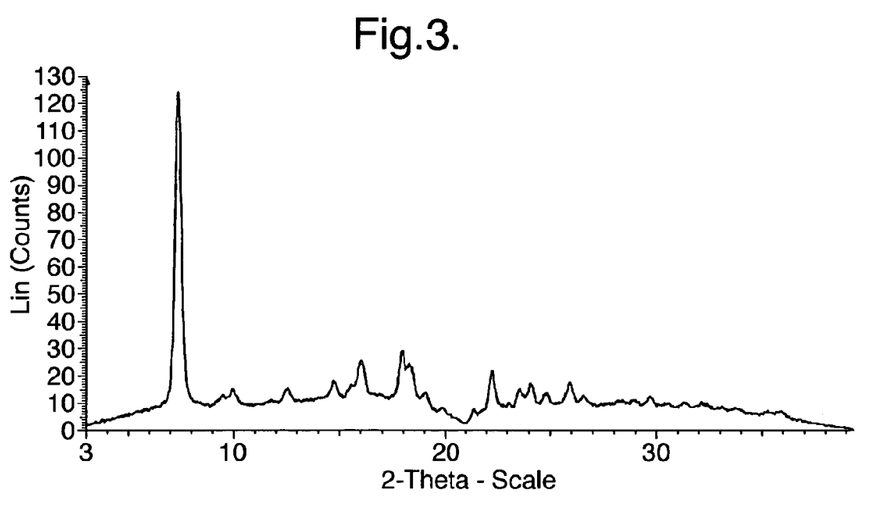
FIG. 3 shows the XRPD-diffractogram of Crystalline Form A of the oxalate salt of Compound I.

The Crystalline Form A of the oxalate salt of Compound I is characterised in that it provides an X-ray powder diffraction pattern substantially as shown in FIG. 3.

The most prominent X-ray powder diffraction peaks for the Crystalline Form A of the oxalate salt of Compound I are shown in Table 3:

TABLE 3

The most prominent peaks of Crystalline
Form A of the oxalate salt of Compound I

| 2-Theta in deg | d value in Angstrom | Intensity* |
|---|---|---|
| 7.3 | 12.025 | Strong |
| 9.9 | 8.921 | Small |
| 12.5 | 7.051 | Small |
| 14.7 | 6.022 | Small |
| 16.02 | 5.529 | Medium |
| 17.97 | 4.930 | Small |
| 18.3 | 4.840 | Medium |
| 21.4 | 4.155 | Small |
| 22.3 | 3.991 | Medium |
| 23.5 | 3.774 | Small |
| 25.9 | 3.434 | Small |

*peak intensities were assigned as follows: Small = 1% to 19.9% the intensity of the most intense peak; Medium = 20% to 79.9% the intensity of the most intense peak; and Strong 80% or above of the intensity of the most intense peak According to the present invention there is provided Crystalline Form A of the oxalate salt of Compound I, wherein said Crystalline Form has an X-ray powder diffraction pattern with at least one specific peak at about 2-theta=7.3°.

According to the present invention there is provided Crystalline Form A of the oxalate salt of Compound I, wherein said Crystalline Form has an X-ray powder diffraction pattern with specific peaks at about the values listed in Table 3 above.

According to the present invention there is provided Crystalline Form A of the oxalate salt of Compound I, wherein said Crystalline Form has an X-ray powder diffraction pattern substantially the same as the X-ray powder diffraction pattern shown in FIG. 3.

The Tartrate Salt of Compound I

We have also found that Compound I can be obtained as a tartrate salt, which possesses a number of advantageous pharmaceutical properties (including, for example, good chemical stability).

Therefore, in a first aspect, the present invention provides a tartrate salt of Compound I.

The tartrate salt of Compound I may exist in a crystalline form.

Suitably, the tartrate salt of Compound I is substantially crystalline.

According to a further aspect, the present invention provides Crystalline Form A of the tartrate salt of compound I.

Figure 4:
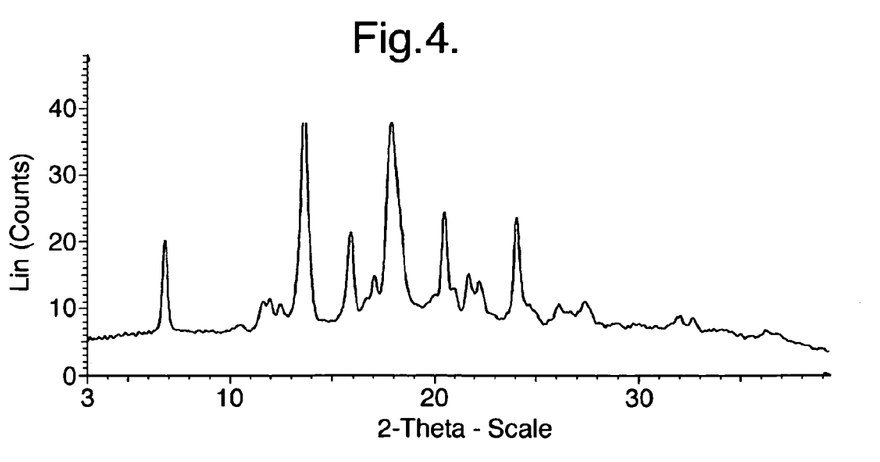
FIG. 4 shows the XRPD-diffractogram of Crystalline Form A of the tartrate salt of Compound I.

The Crystalline Form A of the tartrate salt of Compound I is characterised in that it provides an X-ray powder diffraction pattern substantially as shown in FIG. 4.

The most prominent X-ray powder diffraction peaks for the Crystalline Form A of the tartrate salt of Compound I are shown in Table 4:

TABLE 4

The most prominent peaks of Crystalline
Form A of the tartrate salt of Compound I

| 2-Theta in deg | d value in Angstrom | Intensity* |
|---|---|---|
| 6.8 | 13.033 | Medium |
| 11.6 | 7.601 | Medium |
| 12.0 | 7.386 | Medium |
| 12.5 | 7.097 | Medium |
| 13.6 | 6.498 | Strong |
| 15.9 | 5.565 | Medium |
| 17.1 | 5.186 | Medium |
| 17.9 | 4.959 | Strong |
| 20.5 | 4.327 | Medium |
| 21.7 | 4.090 | Medium |
| 22.3 | 3.988 | Medium |
| 24.1 | 3.692 | Medium |

*peak intensities were assigned as follows: Small = 1% to 19.9% the intensity of the most intense peak; Medium = 20% to 79.9% the intensity of the most intense peak; and Strong 80% or above of the intensity of the most intense peak According to the present invention there is provided Crystalline Form A of the tartrate salt of Compound I, wherein said Crystalline Form has an X-ray powder diffraction pattern with at least one specific peak at about 2-theta=13.6° or 17.9°.

According to the present invention there is provided Crystalline Form A of the tartrate salt of Compound I, wherein said Crystalline Form has an X-ray powder diffraction pattern with specific peaks at about 2-theta=13.6° and 17.9°.

According to the present invention there is provided Crystalline Form A of the tartrate salt of Compound I, wherein said Crystalline Form has an X-ray powder diffraction pattern with at least one specific peak at about 2-theta=6.8°, 13.6°, or 17.9°.

According to the present invention there is provided Crystalline Form A of the tartrate salt of Compound I, wherein said Crystalline Form has an X-ray powder diffraction pattern with specific peaks at about 2-theta=6.8°, 13.6° and 17.9°.

According to the present invention there is provided Crystalline Form A of the tartrate salt of Compound I, wherein said Crystalline Form has an X-ray powder diffraction pattern with specific peaks at about the values listed in Table 4 above.

According to the present invention there is provided Crystalline Form A of the tartrate salt of Compound I, wherein said Crystalline Form has an X-ray powder diffraction pattern substantially the same as the X-ray powder diffraction pattern shown in FIG. 4.

The crystalline forms of the salts of Compound I described herein possess beneficial pharmaceutical properties that make then possible candidates for pharmaceutical development. One such beneficial property could be stability.

The term "stability" as defined herein includes chemical stability and/or solid state stability.

By "chemical stability", we include that the respective compounds can be stored in an isolated form, or in the form of a formulation in which it is provided in admixture with pharmaceutically acceptable carriers, diluents or adjuvants (e.g. in an oral dosage form, such as tablet, capsule etc.), under normal storage conditions, with a limited degree of chemical degradation or decomposition.

By "solid state stability", we include that the respective compounds can be stored in an isolated solid form, or in the form of a solid formulation in which it is provided in admixture with pharmaceutically acceptable carriers, diluents or adjuvants (e.g. in an oral dosage form, such as tablet, capsule etc.), under normal storage conditions, with an to insignificant degree of solid state transformation (e.g. crystallisation, recrystallisation, solid state phase transition, hydration, dehydration, solvation or desolvation).

It is known in the art that an X-ray powder diffraction pattern may be obtained which has one or more measurement errors depending on measurement conditions (such as equipment, sample preparation or machine used). In particular, it is generally known that is intensities in an X-ray powder diffraction pattern may fluctuate depending on measurement conditions and sample preparation. For example, persons skilled in the art of X-ray powder diffraction will realise that the relative intensity of peaks can be affected by, for example, grains above 30 microns in size and non-unitary aspect ratios, which may affect analysis of samples. The skilled person will also realise that the position of reflections can be affected by the precise height at which the sample sits in the diffractometer and the zero calibration of the diffractometer. The surface planarity of the sample may also have a small effect. Hence a person skilled in the art will appreciate that the diffraction pattern data presented herein is not to be construed as absolute (for further information see Jenkins, R & Snyder, R. L. 'Introduction to X-Ray Powder Diffractometry' John Wiley & Sons, 1996). Therefore, it shall be understood that the crystalline forms of the salts of Compound I defined herein of the present invention are not limited to the crystals that provide X-ray powder diffraction patterns identical to the X-ray powder diffraction patterns shown in the accompanying Figures and any crystals providing X-ray powder diffraction patterns substantially the same as that shown in Figures fall within the scope of the present invention. A person skilled in the art of X-ray powder diffraction is able to judge the substantial identity of X-ray powder diffraction patterns.

In the preceding paragraphs defining the X-ray powder diffraction peaks for the crystalline forms of the salts of Compound I defined herein, the term "at about" is used in the expression " . . . at about 2-theta= . . . " to indicate that the precise position of peaks (i.e. the recited 2-theta angle values) should not be construed as being absolute values. It is also stated in the preceding paragraphs that the crystalline forms of the salts of compound I defined herein provide X-ray powder diffraction patterns 'substantially' the same as the X-ray powder diffraction patterns shown in the accompanying figures. It shall be appreciated that the use of the term 'substantially' in this context is also intended to indicate that the 2-theta angle values of the X-ray powder diffraction patterns may vary slightly as to consequence of the inherent experimental variations that can occur with these measurements. Consequently, the peaks traces shown in the Figures cannot be construed as absolute.

Generally, a measurement error of a diffraction angle in an X-ray powder diffractogram is about 2-theta=0.2° or less and such degree of a measurement error should be taken into account when considering the X-ray powder diffraction pattern data described herein. Therefore, where it is stated, for example, that the crystalline form has an X-ray powder diffraction pattern with at least one specific peak at about 2-theta=15.2° then this can be interpreted as being 2-theta=15.2° plus or minus 0.2°.

Process of Preparation

According to a further aspect of the invention, there is provided a method of preparing a salt of Compound I (including a crystalline form thereof) as defined herein, said method comprising the step of reacting the free base of Compound I with the corresponding acid in the presence of a suitable solvent or mixture of solvents.

Therefore, in particular aspect of the invention, there is provided a method of preparing a hydrochloride salt of Compound I (including a crystalline form thereof) as defined herein, said method comprising the step of reacting the free base of Compound I with hydrochloric acid in the presence of a suitable solvent or mixture of solvents.

In a further aspect of the invention, there is provided a method of preparing a malate salt of Compound I (including a crystalline form thereof) as defined herein, said method comprising the step of reacting the free base of Compound I with malic acid in the presence of a suitable solvent or mixture of solvents.

In a further aspect of the invention, there is provided a method of preparing a oxalate salt of Compound I (including a crystalline form thereof) as defined herein, said method comprising the step of reacting the free base of Compound I with oxalic acid in the presence of a suitable solvent or mixture of solvents.

In a further aspect of the invention, there is provided a method of preparing a tartrate salt of Compound I (including a crystalline form thereof) as defined herein, said method comprising the step of reacting the free base of Compound I with tartaric acid in the presence of a suitable solvent or mixture of solvents.

The free base of Compound I can be prepared according to the procedure set out in Example 3 of WO2004/103306.

Any suitable solvent or mixture of solvents may be used to form the salts of compound I defined herein.

A particularly suitable solvent is ethanol.

A person skilled in the art will be able to select appropriate reaction times and conditions for carrying out the salt formation reaction.

Suitably, the free base of compound I is dissolved together with the corresponding acid in a suitable solvent (such as those described in the accompanying examples). Alternatively, a solution of free base of Compound I may be dissolved in a suitable solvent and mixed with a solution of the corresponding acid (which is dissolved in either the same or a compatible solvent). Suitably, the solution is stirred to facilitate mixing of the free base of Compound I and the corresponding acid. The solution may be mixed at ambient temperature although the procedure may also be performed at higher temperatures.

The salts of Compound I defined herein may be isolated using techniques which are well known to those skilled in the art, for example decanting, filtering or centrifuging. Suitably, the salt is collected by filtration.

The method may additionally comprise the further steps of washing the salt of Compound I with a suitable solvent; and drying the salt. Preferably the washed salt is dried under vacuum. It will be appreciated by the skilled person that drying temperature and drying time may affect the solid state properties of compounds that are in the form of solvates (e.g. desolvation may occur at elevated temperatures and/or reduced pressure).

Further experimental details are provided in the Examples.

Pharmaceutical Preparations and Medical Uses

In accordance with the invention, a salt of Compound I (including a crystalline form thereof) as defined herein may be administered orally, intravenously, subcutaneously, buccally, rectally, dermally, nasally, tracheally, bronchially, by any other parenteral route, or via inhalation, in the form of a pharmaceutical preparation comprising a salt of Compound I (including a crystalline form thereof) as defined herein in a pharmaceutically acceptable dosage form.

Typically, therefore, a salt of Compound I (including a crystalline form thereof) as defined herein may be administered orally or parenterally ("parenterally" as used herein, to refers to modes of administration which include intravenous, intramuscular, intraperitoneal, intrasternal, subcutaneous and intraarticular injection and infusion) to a host. In the case of larger animals, such as humans, a salt of Compound I (including a crystalline form thereof) as defined herein may be administered alone as an alternative to administration as compositions in combination with pharmaceutically acceptable diluents, excipients or carriers.

Depending on the disorder, and the patient to be treated, as well as the route of administration, a salt of Compound I (including a crystalline form thereof) as defined herein may be administered at varying doses (see below).

A salt of Compound I (including a crystalline form thereof) as defined herein may be further processed before formulation into a suitable pharmaceutical formulation, for example they may be milled or ground into smaller particles.

According to a further aspect of the invention, there is provided a pharmaceutical composition comprising a salt of Compound I (including a crystalline form thereof) as defined herein in admixture with a pharmaceutically acceptable adjuvant, diluent or carrier.

The amount of a salt of Compound I (including a crystalline form thereof) which is employed in such a composition will depend on the condition, and patient, to be treated, but this can be determined non-inventively.

Pharmaceutical compositions of this invention for parenteral injection suitably comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants.

These compositions may also contain adjuvants such as preservative, wetting agents, emulsifying agents and dispersing agents. Prevention of the action of microorganisms may be ensured by the inclusion of various antibacterial and antifungal agents, for example, paraben, chlorobutanol or phenol sorbic acid. It may also be desirable to include isotonic agents such as sugars or sodium chloride, for example. Prolonged absorption of the injectable pharmaceutical form may be brought about by the inclusion of agents (for example aluminum monostearate and gelatin) which delay absorption.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are suitably made by forming microencapsule matrices of the drug in biodegradable polymers, for example polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations may also prepared by entrapping the drug in liposomes or micro emulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use.

Solid dosage forms for oral administration include capsules, tablets, pills, powders and granules. In such solid dosage forms, a salt of Compound I (including a crystalline form thereof) as defined herein is typically mixed with at least one inert, pharmaceutically acceptable excipient or carrier such as sodium citrate or dicalcium phosphate and/or one or more: a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents. Solid compositions of a similar type may also be employed as fillers in soft and hard-filled gelatin capsules using such excipients as lactose or milk sugar as well as high molecular weight polyethylene glycol, for example.

Suitably, oral formulations contain a dissolution aid. The dissolution aid is not is limited as to its identity so long as it is pharmaceutically acceptable. Examples include nonionic surface active agents, such as sucrose fatty acid esters, glycerol fatty acid esters, sorbitan fatty acid esters (e.g. sorbitan trioleate), polyethylene glycol, polyoxyethylene hydrogenated castor oil, polyoxyethylene sorbitan fatty acid esters, polyoxyethylene alkyl ethers, methoxypolyoxyethylene alkyl ethers, polyoxyethylene alkylphenyl ethers, polyethylene glycol fatty acid esters, polyoxyethylene alkylamines, polyoxyethylene alkyl thioethers, polyoxyethylene polyoxypropylene copolymers, polyoxyethylene glycerol fatty acid esters, pentaerythritol fatty acid esters, propylene glycol monofatty acid esters, polyoxyethylene propylene glycol monofatty acid esters, polyoxyethylene sorbitol fatty acid esters, fatty acid alkylolamides, and alkylamine oxides; bile acid and salts thereof (e.g. chenodeoxycholic acid, cholic acid, deoxycholic acid, dehydrocholic acid and salts thereof, and glycine or taurine conjugate thereof); ionic surface active agents, such as sodium laurylsulfate, fatty acid soaps, alkylsulfonates, alkylphosphates, ether phosphates, fatty acid salts of basic amino acids; triethanolamine soap, and alkyl quaternary ammonium salts; and amphoteric surface active agents, such as betaines and aminocarboxylic acid salts.

The solid dosage forms of tablets, dragees, capsules, pills, and granules can be prepared with coatings and shells such as enteric coatings and other coatings well known in the pharmaceutical formulating art. They may optionally contain opacifying agents and may also be of a composition such that they release the active ingredient(s) only, or preferentially, in a certain part of the intestinal tract, and/or in delayed fashion. Examples of embedding compositions include polymeric substances and waxes.

A salt of Compound I (including a crystalline form thereof) as defined herein may also be in micro-encapsulated form, if appropriate, with one or more of the above-mentioned excipients.

A salt of Compound I (including a crystalline form thereof) as defined herein may be in finely divided form, for example it may be micronised.

Liquid dosage forms for oral administration include pharmaceutically acceptable emulsions, solutions, suspensions, syrups and elixirs. In addition to a salt of Compound I (including a crystalline form thereof) as defined herein, the liquid dosage forms may contain inert diluents commonly used in the art such as water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan and mixtures thereof. Besides inert diluents, the oral compositions may also include adjuvants such as wetting agents, emulsifying and suspending agents, sweetening, flavoring and perfuming agents. Suspensions, in addition to the active compounds, may contain suspending agents such as ethoxylated isostearyl alcohols, polyoxyethylene sorbitol and sorbitan esters, microcrystalline cellulose, aluminum metahydroxide, bentonite, agar-agar, and tragacanth and mixtures thereof.

Compositions for rectal or vaginal administration are preferably suppositories which can be prepared by mixing a salt of Compound I (including a crystalline form thereof) as defined herein with suitable non-irritating excipients or carriers such as cocoa butter, polyethylene glycol or a suppository wax which are solid at room temperature but liquid at body temperature and therefore melt in the rectum or vaginal cavity and release the active compound.

A salt of Compound I (including a crystalline form thereof) as defined herein can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolisable lipid capable of forming liposomes can be used. The present compositions in liposome form can contain, in addition to a compound of the present invention, stabilisers, preservatives, excipients and the like. The preferred lipids are the phospholipids and the phosphatidyl cholines (lecithins), both natural and synthetic. Methods to form liposomes are known in the art, for example, Prescott, Ed., Methods in Cell Biology, Volume XIV, Academic Press, New York, N.Y. (1976), p 33 et seq.

Advantageously, a salt of Compound I (including a crystalline form thereof) as defined herein may be orally active, have rapid onset of activity and low toxicity.

The actual dosage levels of a salt of Compound I (including a crystalline form thereof) as defined herein in the pharmaceutical compositions of this invention may be varied so as to obtain an amount of the active drug that is effective to achieve the desired therapeutic response for a particular patient, compositions, and mode of administration. The selected dosage level will depend upon the activity of the compound, the route of administration, the severity of the condition being treated and the condition and prior medical history of the patient being treated. However, it is within the skill of the art to start doses of the compound at levels lower than required in order to achieve the desired therapeutic effect and to gradually increase the dosage until the desired effect is achieved.

WO2004/103306 discloses Compound I of the present invention in Example 3 (at page 29, lines 1 to 15) and it is also mentioned as one of a list of preferred compounds at page 8, line 19, to page 11, line 28. Furthermore, WO20041103306 also teaches that the compounds described therein are effective inhibitors of EDG receptors and accordingly are useful agents for treating diseases associated with lymphocyte interactions where an alteration in EDG receptor activity contributes to the pathology or symptomology of the disease.

Accordingly, a salt of Compound I (including a crystalline form thereof) as defined herein is, therefore, useful in the therapy of diseases or disorders mediated by lymphocyte interactions, such as, for example, in transplantation, such as acute or chronic rejection of cell, tissue or organ allo- or xenografts or delayed graft function, graft versus host disease; autoimmune diseases, e.g. rheumatoid arthritis, systemic lupus erythematosus, hashimoto's thyroidis, multiple sclerosis, myasthenia gravis, diabetes type I or II and the disorders associated therewith, vasculitis, pernicious anemia, Sjoegren syndrome, uveitis, psoriasis, Graves ophthalmopathy, alopecia areata and others; allergic diseases, e.g. allergic asthma, atopic dermatitis, allergic rhinitis/conjunctivitis, allergic contact dermatitis; inflammatory diseases optionally with underlying aberrant reactions, e.g. inflammatory bowel disease, Crohn's disease or ulcerative colitis, intrinsic asthma, inflammatory lung injury, inflammatory liver injury, inflammatory glomerular injury, atherosclerosis, osteoarthritis, irritant contact dermatitis and further eczematous dermatitises, seborrhoeic dermatitis, cutaneous manifestations of immunologically-mediated disorders, inflammatory eye disease, keratoconjunctivitis, inflammatory myopathy; myocarditis or hepatitis; ischemia/reperfusion injury, e.g. myocardial infarction, stroke, gut ischemia, renal failure or hemorrhage shock, traumatic shock; T cell lymphomas or T cell leukemias; infectious diseases, e.g. toxic shock (e.g. superantigen induced), septic shock, adult respiratory distress syndrome or viral infections, e.g. AIDS, viral hepatitis, chronic bacterial infection; muscle diseases, e.g. polymyositis; or senile dementia. Examples of cell, tissue or solid organ transplants include e.g. pancreatic islets, stem cells, bone marrow, corneal tissue, neuronal tissue, heart, lung, combined heart-lung, kidney, liver, bowel, pancreas, trachea or oesophagus. For the above uses the required dosage will of course vary depending on the mode of administration, the particular condition to be treated and the effect desired.

Furthermore, a salt of Compound I (including a crystalline form thereof) as defined herein is potentially useful in cancer chemotherapy, particularly for cancer chemotherapy of solid tumors, e.g. breast cancer, or as an anti-angiogenic agent.

In addition, a salt of Compound I (including a crystalline form thereof) as defined herein may be useful in the therapy of a variety of peripheral neuropathies, particularly acute or chronic demyelinating neuropathies. A salt of Compound I (including a crystalline form thereof) as defined herein may therefore be useful in the therapy of one or more of Guillain-Barré syndrome (GBS), chronic inflammatory demyelinating polyradiculoneuropathy (CIDP), multifocal motor neuropathy with conduction block (MMN), and paraproteinaemic demyelinating peripheral neuropathy (PDN). In particular, the neuropathy is CIPD. The effectiveness of the compounds may vary between patients.

A salt of Compound I (including a crystalline form thereof) as defined herein is potentially useful for treating multiple sclerosis, uveitis, inflammatory bowel disease, Crohn's disease, ulcerative colitis, infectious diseases (e.g. viral infections), chronic inflammatory demyelinating polyradiculoneuropathy (CIPD) and polymyositis.

The therapeutic use of the compound may include prophylactic use to prevent, control or reduce the severity of a peripheral neuropathy which the subject is at risk of suffering, as well as treatment to control or reduce the severity of existing disease. A salt of Compound I (including a crystalline form thereof) as defined herein may be administered before the onset of symptoms or it may be administered after the onset of symptoms. It may be administered to a subject at risk of suffering a peripheral neuropathy.

The treatments for which a salt of Compound I (including a crystalline form thereof) as defined herein may be used may therefore improve, maintain or delay the deterioration of the medical condition and/or comfort of a patient having, suspected of having, or at risk of having, a peripheral neuropathy.

The term "therapy" includes treatment to alleviate one or more symptoms of a peripheral neuropathy or to delay progression of such a disease; it also includes treatment to cure such a disease, to put a subject into a functional state and/or maintain a subject in a functional state, or to prolong time to relapse.

The required dosage will of course vary depending on the mode of administration, the particular condition to be treated and the effect desired. In general, satisfactory results are indicated to be obtained systemically at daily dosages of between about 0.01 to 500 mg per kg patient body weight per day which can be administered in single or multiple doses. The dosage level may be about 0.1 to about 250 mg/kg per day; e.g. about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions may be provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0 or 1000.0 milligrams of the active ingredient. The compounds may be administered on a regimen of 1 to 4 times per day, preferably once or twice per day. The dosage regimen may be adjusted to provide the optimal therapeutic response.

In accordance with the foregoing the present invention further provides:

1.01 A method for preventing or treating disorders or diseases mediated by lymphocytes, e.g. such as indicated above, in a subject in need of such treatment, which method comprises administering to said subject an effective amount of a salt of Compound I (including a crystalline form thereof) as defined herein;

1.02 A method for preventing or treating organ or tissue transplant rejection, graft versus host disease, autoimmune diseases, allergic diseases, inflammatory diseases or conditions, or muscle diseases in a subject in need of such treatment, which method comprises administering to said subject an effective amount of a salt of Compound I (including a crystalline form thereof) as defined herein;

1.03 A method for preventing or treating acute or chronic transplant rejection or T-cell mediated inflammatory or autoimmune diseases, e.g. as indicated above, in a subject in need of such treatment, which method comprises administering to said subject an effective amount of a salt of Compound I (including a crystalline form thereof) as defined herein;

1.04 A method for inhibiting or controlling deregulated angiogenesis, e.g. sphingosine-I-phosphate (SIP) mediated angiogenesis, in a subject in need thereof, comprising administering to said subject a therapeutically effective amount of a salt of Compound I (including a crystalline form thereof) as defined herein;

1.05 A method for preventing or treating diseases mediated by a neo-angiogenesis process or associated with deregulated angiogenesis in a subject in need thereof, comprising administering to said subject a therapeutically effective amount of a salt of Compound I (including a crystalline form thereof) as defined herein;

1.06 A method for preventing or treating cancer in a subject in need thereof, comprising administering to said subject a therapeutically effective amount of a salt of Compound I (including a crystalline form thereof) as defined herein;

1.07 A method for preventing or treating a peripheral neuropathy in a subject in need thereof, comprising administering to said subject a therapeutically effective amount of a salt of Compound I (including a crystalline form thereof) as defined herein;

1.08 A method for preventing or treating a peripheral neuropathy selected from Guillain-Barré syndrome, chronic inflammatory demyelinating polyradiculoneuropathy (CIPD), multifocal motor neuropathy with conduction block, and paraproteinaemic demyelinating peripheral neuropathy, in a subject in need thereof, comprising administering to said subject a therapeutically effective amount of a salt of Compound I (including a crystalline form thereof) as defined herein;

1.09 A method for preventing or treating chronic inflammatory demyelinating polyradiculoneuropathy (CIPD) in a subject in need thereof, comprising administering to said subject a therapeutically effective amount of a salt of Compound I (including a crystalline form thereof) as defined herein;

1.10 A method for preventing or treating multiple sclerosis in a subject in need thereof, comprising administering to said subject a therapeutically effective amount a salt of Compound I (including a crystalline form thereof) as defined herein;

1.11 A method for preventing or treating uveitis in a subject in need thereof, comprising administering to said subject a therapeutically effective amount of a salt of Compound (including a crystalline form thereof) as defined herein;

1.12 A method for preventing or treating inflammatory bowel disease, Crohn's disease or ulcerative colitits in a subject in need thereof, comprising administering to said subject a therapeutically effective amount of a salt of Compound I (including a crystalline form thereof) as defined herein;

1.13 A method for preventing or treating inflammatory bowel disease in a subject in need thereof, comprising administering to said subject a therapeutically effective amount of a salt of Compound I (including a crystalline form thereof) as defined herein;

1.14 A method for preventing or treating Crohn's disease in a subject in need thereof, comprising administering to said subject a therapeutically effective amount of a salt of Compound I (including a crystalline form thereof) as defined herein;

1.15 A method for preventing or treating ulcerative colitits in a subject in need thereof, comprising administering to said subject a therapeutically effective amount of a salt of Compound I (including a crystalline form thereof) as defined herein;

1.16 A method for preventing or treating infectious diseases (e.g. viral infections) in a subject in need thereof, comprising administering to said subject a therapeutically effective amount of a salt of Compound I (including a crystalline form thereof) as defined herein;

1.17 A method for preventing or treating viral infections in a subject in need thereof, comprising administering to said subject a therapeutically effective amount of a salt of Compound I (including a crystalline form thereof) as defined herein;

1.18 A method for preventing or treating polymyositis in a subject in need thereof, comprising administering to said subject a therapeutically effective amount of a salt of Compound I (including a crystalline form thereof) as defined herein;

2. A salt of Compound I (including a crystalline form thereof) as defined herein for use as a pharmaceutical 2.1 A salt of Compound I (including a crystalline form thereof) as defined herein, for use as a pharmaceutical in any of the methods defined in paragraphs 1.01 to 1.18 above, or for the treatment of any one of the medical conditions mentioned hereinbefore;

3. A pharmaceutical composition, e.g. for use in any of the methods defined in paragraphs 1.01 to 1.18 above or for the treatment of any one of the medical conditions mentioned hereinbefore, comprising a salt of Compound I (including a crystalline form thereof) as defined herein in association with a pharmaceutically acceptable diluent or carrier therefor.

4. A salt of Compound I (including a crystalline form thereof) as defined herein, for use in the preparation of a pharmaceutical composition for use in any of the methods defined in paragraphs 1.01 to 1.18 above or for the treatment of any one of the medical conditions mentioned hereinbefore.

The present invention also relates to the use of a salt of Compound I (including a crystalline form thereof) as defined herein in the manufacture of a medicament for use in the treatment of any one of the medical conditions mentioned hereinbefore or in paragraphs 1.01 to 1.18 above.

Combination Therapies

The salts of Compound I (including any crystalline forms thereof) defined herein may be administered as the sole active ingredient or in conjunction with, e.g. as an adjuvant to, other drugs, such as, for example, immunosuppressive or immunomodulating agents or other anti-inflammatory agents in the treatment or prevention of alto- or xenograft acute or chronic rejection or inflammatory or autoimmune disorders; or a chemotherapeutic agent for the treatment of cancer, such as, for example, a malignant cell anti-proliferative agent. For example, the salts of Compound I (including any crystalline forms thereof) as defined herein may be used in combination with a calcineurin inhibitor, e.g. cyclosporin A or FK 506; a mTOR inhibitor, e.g. rapamycin, 40-0-(2-hydroxyethyl)-rapamycin, CCI779, ABT578 or AP23573; an ascomycin having immunosuppressive properties, e.g. ABT-281, ASM981, etc.; corticosteroids; cyclophosphamide; azathioprene; methotrexate; leflunomide; mizoribine; mycophenolic acid; mycophenolate mofetil; 15-deoxyspergualine or an immunosuppressive homologue, analogue or derivative thereof; immunosuppressive monoclonal antibodies, e.g. monoclonal antibodies to leukocyte receptors, e.g. MHC, CD2, CD3, CD4, CD7, CD8, CD25, CD28, CD40. CD45, CD58, CD80, CD86 or their ligands; other immunomodulatory compounds, e.g. a recombinant binding molecule having at least a portion of the extracellular domain of CTLA4 or a mutant thereof, e.g. an at least extracellular portion of CTLA4 or a mutant thereof joined to a non-CTLA4 protein sequence, e.g. CTLA4Ig (for ex. designated ATCC 5 68629) or a mutant thereof, e.g. LEA29Y; adhesion molecule inhibitors, e.g. LFA-I antagonists, ICAM-1 or -3 antagonists, VCAM-4 antagonists or VLA-4 antagonists; or a chemotherapeutic agent.

By the term "chemotherapeutic agent" is meant any chemotherapeutic agent and it includes but is not limited to,
  i. an aromatase inhibitor,
  ii. an anti-estrogen, an anti-androgen (especially in the case of prostate cancer) or a gonadorelin agonist,
  iii. a topoisomerase I inhibitor or a topoisomerase II inhibitor,
  iv. a microtubule active agent, an alkylating agent, an anti-neoplastic antimetabolite or a platin compound,
  v. a compound targeting/decreasing a protein or lipid kinase activity or a protein or lipid phosphatase activity, a further anti-angiogenic compound or a compound which induces cell differentiation processes,
  vi. a bradykinin I receptor or an angiotensin II antagonist,
  vii. a cyclooxygenase inhibitor, a bisphosphonate, a histone deacetylase inhibitor, a heparinase inhibitor (prevents heparan sulphate degradation), e.g. PI-88, a biological response modifier, preferably a lymphokine or interferons, e.g. interferon γ, an ubiquitination inhibitor, or an inhibitor which blocks anti-apoptotic pathways,
  viii. an inhibitor of Ras oncogenic isoforms, e.g. H-Ras, K-Ras or N-Ras, or a farnesyl transferase inhibitor, e.g. L-744,832 or DK8G557,
  ix. a telomerase inhibitor, e.g. telomestatin,
  x. a protease inhibitor, a matrix metalloproteinase inhibitor, a methionine aminopeptidase inhibitor, e.g. bengamide or a derivative thereof, or a proteosome inhibitor, e.g. PS-341, and/or
  xi. a mTOR inhibitor.

The term "aromatase inhibitor" as used herein relates to a compound which inhibits the estrogen production, i.e. the conversion of the substrates androstenedione and testosterone to estrone and estradiol, respectively. The term includes, but is not limited to to steroids, especially atamestane, exemestane and formestane and, in particular, non-steroids, especially amino glutethimide, roglethimide, pyridoglutethimide, trilostane, testolactone, ketokonazole, vorozole, fadrozole, anastrozole and letrozole. A combination of the invention comprising a chemotherapeutic agent which is an aromatase inhibitor is particularly useful for the treatment of hormone receptor positive tumors, e.g. breast is tumors.

The term "anti-estrogen" as used herein relates to a compound which antagonizes the effect of estrogens at the estrogen receptor level. The term includes, but is not limited to tamoxifen, fulvestrant, raloxifene and raloxifene hydrochloride. A combination of the invention comprising a chemotherapeutic agent which is an anti-estrogen is particularly useful for the treatment of estrogen receptor positive tumors, e.g. breast tumors.

The term "anti-androgen" as used herein relates to any substance which is capable of inhibiting the biological effects of androgenic hormones and includes, but is not limited to, bicalutamide.

The term "gonadorelin agonist" as used herein includes, but is not limited to abarelix, goserelin and goserelin acetate.

The term "topoisomerase I inhibitor" as used herein includes, but is not limited to topotecan, irinotecan, 9-nitrocamptothecin and the macromolecular camptothecin conjugate PNU-166148 (compound A 1 in WO99/17804).

The term "topoisomerase II inhibitor" as used herein includes, but is not limited to the anthracyclines such as doxorubicin, daunorubicin, epirubicin, idarubicin and nemorubicin, the anthraquinones mitoxantrone and losoxantrone, and the podophillotoxines etoposide and teniposide.

The term "microtubule active agent" relates to microtubule stabilizing and microtubule destabilizing agents including, but not limited to taxanes, e.g. paclitaxel and docetaxel, vinca alkaloids, e.g., vinblastine, especially vinblastine sulfate, vincristine especially vincristine sulfate, and vinorelbine, discodennolides and epothilones and derivatives thereof, e.g. epothilone B or a derivative thereof.

The term "alkylating agent" as used herein includes, but is not limited to busulfan, chlorambucil, cyclophosphamide, ifosfamide, melphalan or nitrosourea (BCNU or Gliadel™).

The term "antineoplastic antimetabolite" includes, but is not limited to 5-fluorouracil, capecitabine, gemcitabine, cytarabine, fludarabine, thioguanine, methotrexate and edatrexate.

The term "platin compound" as used herein includes, but is not limited to carboplatin, cis-platin and oxaliplatin.

The term "compounds targeting/decreasing a protein or lipid kinase activity or is further anti-angiogenic compounds" as used herein includes, but is not limited to, protein tyrosine kinase and/or serine and/or threonine kinase inhibitors or lipid kinase inhibitors, e.g. compounds targeting, decreasing or inhibiting the activity of the epidermal growth factor family of receptor tyrosine kinases (EGFR, ErbB2, ErbB3, ErbB4 as homo- or heterodimers), the vascular endothelial growth factor family of receptor tyrosine kinases (VEGFR), the platelet-derived growth factor-receptors (PDGFR), the fibroblast growth factor-receptors (FGFR), the insulin-like growth factor receptor 1 (IGF-IR), the Trk receptor tyrosine kinase family, the Axl receptor tyrosine kinase family, the Ret receptor tyrosine kinase, the KitlSCFR receptor tyrosine kinase, members of the c-Abl family and their genefusion products (e.g. BCR-Abl), members of the protein kinase C (PKC) and Raf family of serine/threonine kinases, members of the MEK, SRC, JAK, FAK, PDK or PI(3) kinase family, or of the PI(3)-kinase-related kinase family, and/or members of the cyclin-dependent kinase family (CDK) and anti-angiogenic compounds having another mechanism for their activity, e.g. unrelated to protein or lipid kinase inhibition.

Compounds which target, decrease or inhibit the activity of VEGFR are especially compounds, proteins or antibodies which inhibit the VEGF receptor tyrosine kinase, inhibit a VEGF receptor or bind to VEGF, and are in particular those compounds, proteins or monoclonal antibodies generically and specifically disclosed in WO 98/35958, e.g. 1-(4-chloroanilino)-4-(4-pyridylmethyl)phthalazine or a pharmaceutically acceptable salt thereof, e.g. the succinate, in WO 00127820, e.g. a N-aryl(thio) anthranilic acid amide derivative e.g. 2-[(4-pyridyl)methyl]amino-N-[3-methoxy-5-(trifluoromethyl) phenyl]benzamide or 2-[(1-oxido-4-pyridyl) methyl]amino-N-[3-trifluoromethylphenyl]benzamide, or in WO 00/09495, WO 00/159509, WO 98/11223, WO 00/27819 and EP 0 769 947; those as described by M. Prewett et al in Cancer Research 59 (1999) 5209-5218, by F. Yuan et al in Proc. Natl. Acad. Sci. USA, vol. 93, pp. 14765-14770, December 1996, by Z. Zhu et al in Cancer Res. 58, 1998, 3209-3214, and by J. Mordenti et al in Toxicologic Pathology, Vol. 27, no. 1, pp 14-21, 1999; in WO 00/37502 and WO 94/10202; Angiostatin™, described by M. S. O'Reilly et al, Cell 79, 1994, 315-328; Endostatin™, described by M. S. O'Reilly et al, Cell 88, 1997, 277-285; anthranilic acid amides; ZD4190; ZD6474; SU5416; SU6668; or anti-VEGF antibodies or anti-VEGF receptor antibodies, e.g. RhuMab.

By antibody is meant intact monoclonal antibodies, polyclonal antibodies, multispecific antibodies formed from at least 2 intact antibodies, and antibody fragments so long as they exhibit the desired biological activity.

Compounds which target, decrease or inhibit the activity of the epidermal growth factor receptor family are especially compounds, proteins or antibodies which inhibit members of the EGF receptor tyrosine kinase family, e.g. EGF receptor, ErbB2, ErbB3 and ErbB4 or bind to EGF or EGF related ligands, or which have a dual inhibiting effect on the ErbB and VEGF receptor kinase and are in particular those compounds, proteins or monoclonal antibodies generically and specifically disclosed in WO 97/02266, e.g. the compound of ex. 39, or in EP 0 564 409, WO 99/03854, EP 0520722, EP 0 566 226, EP 0 787 722, EP 0 837 063, U.S. Pat. No. 5,747,498, WO 98/10767, WO 97/30034, WO 97/49688, WO 97/38983 and, especially, WO 96/30347 (e.g. compound known as CP 358774), WO 96/33980 (e.g. compound ZD 1839) and WO 95103283 (e.g. compound ZM105180) or PCT/EP02/08780; e.g. trastuzumab (Herpetin®), cetuximab, Iressa, OSI-774, CI-1033, EKB-569, GW-2016, E1.1, E2.4, E2.5, E6.2, E6.4, E2.11, E6.3 or E7.6.3.

Compounds which target, decrease or inhibit the activity of PDGFR are especially compounds which inhibit the PDGF receptor, e.g. a N-phenyl-2-pyrimidine-amine derivative, e.g. imatinib.

Compounds which target, decrease or inhibit the activity of c-Abl family members and their gene fusion products are, e.g. a N-phenyl-2-pyrimidine-amine derivative, e.g. imatinib; PD180970; AG957; or NSC 680410.

Compounds which target, decrease or inhibit the activity of protein kinase C, Raf, MEK, SRC, JAK, FAK and PDK family members, or PI(3) kinase or PI(3) kinase-related family members, and/or members of the cyclin-dependent kinase family (CDK) are especially those staurosporine derivatives disclosed in EP 0 296 110, e.g. midostaurin; examples of further compounds include e.g. UCN-Ol, safingol, BAY 43-9006, Bryostatin 1, Perifosine; Ilmofosine; RO 318220 and RO 320432; GO 6976; Isis 3521; or LY333531/LY379196.

Further anti-angiogenic compounds are e.g. thalidomide (THALOMID) and TNP-470.

Compounds which target, decrease or inhibit the activity of a protein or lipid phosphatase are, e.g. inhibitors of phosphatase 1, phosphatase 2A, PTEN or CDC25, e.g. okadaic acid or a derivative thereof.

Compounds which induce cell differentiation processes are, e.g. retinoic acid, α-, γ- or δ-tocopherol or α-, γ- or δ-tocotrienol.

The term cyclooxygenase inhibitor as used herein includes, but is not limited to, e.g. celecoxib (Celebrex®), rofecoxib (Vioxx®), etoricoxib, valdecoxib or a 5-alkyl-2-arylaminophenylacetic acid, e.g. 5-methyl-2-(2'-chloro-6'-fluoroanilino)phenyl acetic acid.

The term "histone deacetylase inhibitor" as used herein includes, but is not limited to MS-275, SAHA, pyroxamide, FR-901228 or valproic acid.

The term "bisphosphonates" as used herein includes, but is not limited to, etridonic, clodronic, tiludronic, pamidronic, alendronic, ibandronic, risedronic and zoledronic acid.

The term "matrix metalloproteinase inhibitor" as used herein includes, but is not limited to collagen peptidomimetic and non-petidomimetic inhibitors, tetracycline derivatives, e.g. hydroxamate peptidomimetic inhibitor batimastat and its orally bioavailable analogue marimastat, prinomastat, BMS-279251, BAY 12-9566, TAA211 or AAJ996.

The term "mTOR inhibitor" as used herein includes, but is not limited to rapamycin (sirolimus) or a derivative thereof, e.g. 32-deoxorapamycin, 16-pent-2-ynyloxy-32-deoxorapamycin, 16-pent-2-ynyloxy-32(S)-dihydro-rapamycin, 16-pent-2-ynyloxy-32(S)-dihydro-40-0-(2-hydroxyethyl)-rapamycin and, more preferably, 40-0-(2-hydroxyethyl)-rapamycin. Further examples of rapamycin derivatives include e.g. CCI779 or 40-[3-hydroxy-2-(hydroxymethyl)-2-methylpropanoate]-rapamycin or a pharmaceutically acceptable salt thereof, as disclosed in U.S. Pat. No. 5,362,718, ABT578 or 40-(tetrazolyl)-rapamycin, particularly 40-epi-(tetrazolyl)-rapamycin, e.g. as disclosed in WO 99/15530, or rapalogs as disclosed e.g. in WO 98/02441 and WO0/14387, e.g. AP23573. Where a salt of Compound I is administered in conjunction with other immunosuppressive, immunomodulatory, anti-inflammatory or chemotherapeutic therapy, dosages of the co-administered immunosuppressant, immunomodulatory, anti-inflammatory, or chemotherapeutic compound will of course vary depending on the type of codrug employed, e.g. whether it is a steroid or a calcineurin inhibitor, on the specific drug employed, on the condition being treated and so forth.

For the treatment of peripheral neuropathy a salt of Compound I as defined herein, may be administered with a further therapeutic agent useful for treating a peripheral neuropathy, for example a demyelinating peripheral neuropathy. By way of example, a second therapeutic agent may be an immunosuppresant (e.g., cyclosporin A, cyclosporin G, FK-506, ABT-281, ASM981, rapamycin, 40-O-(2-hydroxy)ethyl-rapamycin, corticosteroids, cyclophosphamide, azathioprine, methotrexate, leflunomide, mizoribine, mycophenolate mofetil, or 15-deoxyspergualine), a steroid (e.g., prednisone or hydrocortisone), an immunoglobulin, or type 1 interferon. A salt of Compound I as defined herein and the second agent can be administered simultaneously or consecutively.

In accordance with the foregoing the present invention provides in a yet further aspect:
5. A method as defined above comprising co-administration, e.g. concomitantly or in sequence, of a therapeutically effective non-toxic amount of a salt of Compound I (including a crystalline form thereof) as defined herein and at least a second drug substance, e.g. an immunosuppressant, immunomodulatory, anti-inflammatory or chemotherapeutic drug, e.g. as indicated above.
6. A pharmaceutical combination, e.g. a kit, comprising a) a first agent which is a salt of Compound I (including a crystalline form thereof) as defined herein, and b) at least one co-agent, e.g. an immunosuppressant, immunomodulatory, anti-inflammatory or chemotherapeutic drug, e.g. as disclosed above.

The kit may comprise instructions for its administration.

The terms "co-administration" or "combined administration" or the like as utilized herein are meant to encompass administration of the selected therapeutic agents to a single patient, and are intended to include treatment regimens in which the agents are not necessarily administered by the same route of administration or at the same time.

The term "pharmaceutical combination" as used herein means a product that results from the mixing or combining of more than one active ingredient and includes both fixed and non-fixed combinations of the active ingredients. The term "fixed combination" means that the active ingredients, e.g. a salt of Compound I (including any crystalline forms thereof) as defined herein and a co-agent, are both administered to a patient simultaneously in the form of a single entity or dosage. The term "non-fixed combination" means that the active ingredients, e.g. a salt of Compound I (including any crystalline forms thereof) as defined herein and a co-agent, are both administered to a patient as separate entities either simultaneously, concurrently or sequentially with no specific time limits, wherein such administration provides therapeutically effective levels of the two compounds in the body of the patient. The latter also applies to cocktail therapy, e.g. the administration of three or more active ingredients.

EXAMPLES

The invention is illustrated, but in no way limited, by the following Examples and with reference to the enclosed Figures.

General Procedures

X-Ray Powder Diffraction
X-ray powder diffraction analysis (XRPD) was performed on samples prepared according to standard methods, for example those described in Giacovazzo, C. et al (1995), *Fundamentals of Crystallography*, Oxford University Press; Jenkins, R. and Snyder, R. L. (1996), *Introduction to X-Ray Powder Diffractometry*, John Wiley & Sons, New York; Bunn, C. W. (1948), *Chemical Crystallography*, Clarendon Press, London; or Klug, H. P. & Alexander, L. E. (1974), *X-ray Diffraction Procedures*, John Wiley and Sons, New York. X-ray analyses were performed using a Bruker D8 Advance Powder X-ray Diffactometer. Samples were analysed as powder and placed as powder on the specimen holder.

XRPD diffraction angles (2-theta) may vary in the range ±0.2° (2-theta).

In some of the following Examples, the same crystalline form is prepared by different processes. In such cases, reference is made to the same representative characterising data because each process produced the same crystalline form having "essentially" the same XRPD diffraction pattern. In other words, it was clear from the relevant patterns (allowing for experimental error) that the same crystalline form had been prepared.

Preparation of Starting Materials
Unless otherwise described herein, the free base form of Compound I may be prepared as described in Example 3 of WO2004/103306.

SUMMARY OF FIGURES

Crystals obtained as described herein were analyzed by XRPD and the results are is tabulated above and are shown in the respective Figures.

EXAMPLE 1

Preparation of the Crystalline Form A of the Hydrochloride Salt of 1-(4-{1-[(E)-4-Cyclohexyl-3-trifluoromethyl-benzyloxyimino]-ethyl}-2-ethyl-benzyl)-azetidine-3-carboxylic acid (Compound I)

Method 1
The free base of Compound I (100 mg) and 1N HCL (193.5 µL) were added to 1 mL of ethanol. The resultant solution was stirred for 72 hours. Acetonitrile (2 mL) was then added and the solution was stirred overnight. The white solid precipitate was collected by vacuum filtration.

Method 2
The free base of Compound I (200 mg) and 1 N HCl (387 µL) were added to 2 ml ethanol. Once the free base of Compound I had dissolved, the solution was evaporated to dryness and formed an amorphous glass. Acetonitrile (4 mL) was added to the amorphous glass product in aliquots while sonicating in a warm water bath for 20 minutes. The resultant solution was then left to stir overnight and the white solid product formed was collected by vacuum filtration.

Analysis of Crystalline Form A of the Hydrochloride Salt of Compound I:

XRPD analysis indicated that the product was Crystalline Form A of the hydrochloride salt of 1-(4-{1-[(E)-4-Cyclohexyl-3-trifluoromethyl-benzyloxyimino]-ethyl}-2-ethyl-benzyl)-azetidine-3-carboxylic acid (Compound I), having the most prominent peaks shown in Table 1 above and an XRPD trace as shown in FIG. 1.

EXAMPLE 2

Preparation of the Crystalline Form A of the Malate Salt of 1-(4-{1-[(E)-4-Cyclohexyl-3-trifluoromethyl-benzyloxyimino]-ethyl}-2-ethyl-benzyl)-azetidine-3-carboxylic acid (Compound I)

Solid malic acid (26 mg) and the free base of Compound 1 (100 mg) were added to 1 mL of ethanol. The solution was stirred for 72 hours and was then evaporated to dryness by nitrogen gas flow to form amorphous glass. Acetonitrile (2 mL) was added to the amorphous glass and the resultant white solid was collected by vacuum filtration.

XRPD analysis indicated that the product was Crystalline Form A of the malate salt of 1-(4-{1-[(E)-4-Cyclohexyl-3-trifluoromethyl-benzyloxyimino]-ethyl}-2-ethyl-benzyl)-azetidine-3-carboxylic acid (Compound I), having the most prominent peaks shown in Table 2 above and an XRPD trace as shown in FIG. 2.

EXAMPLE 3

Preparation of the Crystalline Form A of the Oxalate Salt of 1-(4-{1-[(E)-4-Cyclohexyl-3-trifluoromethyl-benzyloxyimino]-ethyl}-2-ethyl-benzyl)-azetidine-3-carboxylic acid (Compound I)

The free base of Compound I (100 mg) and oxalic acid (17.43 mg) were dissolved in 1 mL of ethanol. The solution was stirred for 72 hours and the precipitate formed was collected by vacuum filtration.

XRPD analysis indicated that the product was Crystalline Form A of the oxalate salt of 1-(4-{1-[(E)-4-Cyclohexyl-3-trifluoromethyl-benzyloxyimino]-ethyl}-2-ethyl-benzyl)-azetidine-3-carboxylic acid (Compound I), having the most prominent peaks shown in Table 3 above and an XRPD trace as shown in FIG. 3.

EXAMPLE 4

Preparation of the Crystalline Form A of the Tartrate Salt of 1-(4-{1-[(E)-4-Cyclohexyl-3-trifluoromethyl-benzyloxyimino]-ethyl}-2-ethyl-benzyl)-azetidine-3-carboxylic acid (Compound I)

Method 1

The free base of Compound I (64.4 mg) was dissolved in a solution of 1 mL of ethanol and 1 mL of 0.125 mM solution of tartaric acid. The solution was stirred overnight and the resultant solids were then collected by vacuum filtration.

Method 2

Tartaric acid (116 mg) was added to 1 mL of ethanol EtOH and heated to 50° C. until it dissolved. The free base of Compound I (400 mg) was then added to this solution. A precipitate formed within 30 minutes. Stirring of the mixture continued for 2 hours and the slurry was cooled in an ice bath for a further 30 minutes. The slurry was then vacuum filtered to collect the white solids.

Method 3

The free base of Compound I (50 mg) and tartaric acid (14.5 mg) were dissolved in 1 mL of ethanol at 40° C. and the solution was stirred for 2 hours. The mixture was then evaporated to dryness to yield an amorphous glass. Acetonitrile (2 mL) was added and the amorphous glass changed to white crystalline powder. The white crystalline powder was collected by vacuum filtration.

XRPD analysis indicated that the product was Crystalline Form A of the tartrate salt of 1-(4-{1-[(E)-4-Cyclohexyl-3-trifluoromethyl-benzyloxyimino]-ethyl}-2-ethyl-benzyl)-azetidine-3-carboxylic acid (Compound I), having the most prominent peaks shown in Table 4 above and an XRPD trace as shown in FIG. 4.

EXAMPLE 5

Hygroscopy of the Crystalline Form A of the Hydrochloride and Tartrate Salts of Compound I Crystalline forms A of the hydrochloride and tartrate salts of Compound I were prepared according to the methodology described in Examples 1 and 4.

The samples were tested for hygroscopy by exposure to an atmosphere of 95% RH. The tartrate salt was found to be slightly hygroscopic, with a moisture uptake of 2.49%. The hydrochloride salt was found to have a low hygroscopy, with a moisture uptake of 0.61%. Neither sample showed any change in XRPD pattern following storage at 93% RH and 25° C. for 1 day.

EXAMPLE 6

Stability of the Crystalline Form A of the Hydrochloride and Tartrate Salts of Compound I Crystalline forms A of the hydrochloride and tartrate salts of Compound I were prepared according to the methodology described in Examples 1 and 4. Stability against temperature and light were then measured as described below.

Temperature stability was tested by measuring decomposition and colour change caused by placing the samples in an airtight container for 1 week at 80° C. (in bulk form and as a 1% component in two mixtures) and in an identical container for 1 week at 80° C. and at a relative humidity of 75%. Where a change in XRPD was observed, the temperature of the phase transition was measured using differential scanning colorimetry (DSC).

Light stability was tested by measuring decomposition and colour change following exposure to the sample to 1200 kiloLuxhours from a Xenon light.

The results are shown in Table 5 below.

TABLE 5

Stability of Crystalline forms A of hydrochloride and tartrate salts of Compound I

| | Form A of hydrochloride salt | | Form A of tartrate salt | |
|---|---|---|---|---|
| | Decomposition products (%) | Discoloration | Decomposition products (%) | Discoloration |
| Unstressed (1 week) | 1.1 | | 0.8 | |
| Solid state, 1 week 80° C., tight container | | | | |
| Bulk (HPLC) | 11.5 | No change in colour | 8.8 | No change in colour |
| Bulk (XRPD, DSC) | No change | | Changed 136.3° C. | |
| 1% in mixture of Lactose 200 mesh (78.5%), corn starch (20%), aerosil 200 (0.5%), magnesium stearate (1%) | 94.8 | Strong discolouration | 23.8 | No change in colour |
| 1% in mixture of Mannitol 60 (50%), avicel PH 101 (43%), crospovidone (5%), aerosil (1%), magnesium stearate (1%) | 92.7 | Strong discolouration | 37.0 | No change in colour |
| Xenon light (approx. 1200 kLuxh) | | | | |
| Bulk (HPLC) | 1.1 | No change in colour | 0.8 | No change in colour |
| Bulk (XRPD) | No change | | No change | |
| Solid state, 1 week 80° C.,/75% relative humidity | | | | |
| Bulk (HPLC) | 91.5 | Strong discolouration | 18.0 | Strong discolouration |
| Bulk (XRPD) | Melted glass | | Melted glass | |
| 1% in mixture of Lactose 200 mesh (78.5%), corn starch (20%), aerosil 200 (0.5%), magnesium stearate (1%) | 95.2 | Strong discolouration | 70.9 | Strong discolouration |
| 1% in mixture of Mannitol 60 (50%), avicel PH 101 (43%), crospovidone (5%), aerosil (1%), magnesium stearate (1%) | 95.8 | Strong discolouration | 93.2 | Medium discolouration |

These results show that both the hydrochloride and tartrate crystal forms exhibit good resistance to decomposition at elevated temperatures. In addition, the tartate form exhibits superior resistance to decomposition under conditions of high humidity and when mixed with representative pharmaceutical compositions.

The invention claimed is:

1. A method of treating disorders or diseases mediated by lymphocytes, in a subject in need of such treatment, the method comprising administering to said subject a pharmaceutical composition comprising a therapeutically effective amount of a hydrochloride salt of 1-(4-{1-[(E)-4-cyclohexyl-3-trifluoromethyl-benzyloxyimino]-ethyl}-2-ethyl-benzyl)-azetidine-3-carboxylic acid, and a pharmaceutically acceptable adjuvant, diluent or carrier.

2. A method according to claim 1, wherein the hydrochloride salt of 1-(4-{1-[(E)-4-cyclohexyl-3-trifluoromethyl-benzyloxyimino]-ethyl}-2-ethyl-benzyl)-azetidine-3-carboxylic acid that is administered is greater than 60% crystalline.

3. A method according to claim 2, wherein the hydrochloride salt of 1-(4-{1-[(E)-4-cyclohexyl-3-trifluoromethyl-benzyloxyimino]-ethyl}-2-ethyl-benzyl)-azetidine-3-carboxylic acid that is administered is greater than 80% crystalline.

4. A method according to claim 3, wherein the hydrochloride salt of 1-(4-{1-[(E)-4-cyclohexyl-3-trifluoromethyl-benzyloxyimino]-ethyl}-2-ethyl-benzyl)-azetidine-3-carboxylic acid that is administered is greater than 90% crystalline.

5. A method of treating organ or tissue transplant rejection, graft versus host disease, autoimmune diseases, allergic diseases, inflammatory diseases or conditions, or muscle diseases in a subject in need of such treatment, the method comprising administering to said subject a pharmaceutical composition comprising a therapeutically effective amount of a hydrochloride salt of 1-(4-{1-[(E)-4-cyclohexyl-3-trifluoromethyl-benzyloxyimino]-ethyl}-2-ethyl-benzyl)-azetidine-3-carboxylic acid and a pharmaceutically acceptable adjuvant, diluent or carrier.

6. A method according to claim 5, wherein the hydrochloride salt of 1-(4-{1-[(E)-4-cyclohexyl-3-trifluoromethyl-benzyloxyimino]-ethyl}-2-ethyl-benzyl)-azetidine-3-carboxylic acid that is administered is greater than 60% crystalline.

7. A method according to claim 6, wherein the hydrochloride salt of 1-(4-{1-[(E)-4-cyclohexyl-3-trifluoromethyl-benzyloxyimino]-ethyl}-2-ethyl-benzyl)-azetidine-3-carboxylic acid that is administered is greater than 80% crystalline.

8. A method according to claim 7, wherein the hydrochloride salt of 1-(4-{1-[(E)-4-cyclohexyl-3-trifluoromethyl-benzyloxyimino]-ethyl}-2-ethyl-benzyl)-azetidine-3-carboxylic acid that is administered is greater than 90% crystalline.

9. A method of treating disorders or diseases mediated by lymphocytes, in a subject in need of such treatment, said method comprising administering to said subject a pharmaceutical composition comprising a therapeutically effective amount of an oxalate salt of 1-(4-{1-[(E)-4-cyclohexyl-3-trifluoromethyl-benzyloxyimino]-ethyl}-2-ethyl-benzyl)- azetidine-3-carboxylic acid and a pharmaceutically acceptable adjuvant, diluent or carrier.

10. A method according to claim 9, wherein the oxalate salt of 1-(4-{1-[(E)-4-cyclohexyl-3-trifluoromethyl-benzyloxyimino]-ethyl}-2-ethyl-benzyl)-azetidine-3-carboxylic acid that is administered Crystalline Form A of said salt, which has an X-ray powder diffraction pattern having at least one specific peak at about 2-theta=7.3°.

11. A method according to claim 10, wherein said Crystalline Form A of the oxalate salt of 1-(4-{1-[(E)-4-cyclohexyl-3-trifluoromethyl-benzyloxyimino]-ethyl}-2-ethyl-benzyl)-azetidine-3-carboxylic acid has an X-ray powder diffraction pattern that is substantially the same as the X-ray powder diffraction pattern shown in FIG. 3.

12. A method of treating organ or tissue transplant rejection, graft versus host disease, autoimmune diseases, allergic diseases, inflammatory diseases or conditions, or muscle diseases in a subject in need of such treatment, the method comprising administering to said subject a pharmaceutical composition comprising a therapeutically effective amount of an oxalate salt of 1-(4-{1-[(E)-4-cyclohexyl-3-trifluoromethyl-benzyloxyimino]-ethyl}-2-ethyl-benzyl)-azetidine-3-carboxylic acid and a pharmaceutically acceptable adjuvant, diluent or carrier.

13. A method according to claim 12, wherein the oxalate salt of 1-(4-{1-[(E)-4-cyclohexyl-3-trifluoromethyl-benzyloxyimino]-ethyl}-2-ethyl-benzyl)-azetidine-3-carboxylic acid that is administered Crystalline Form A of said salt, which has an X-ray powder diffraction pattern having at least one specific peak at about 2-theta=7.3°.

14. A method according to claim 13, wherein said Crystalline Form A of the oxalate salt of 1-(4-{1-[(E)-4-cyclohexyl-3-trifluoromethyl-benzyloxyimino]-ethyl}-2-ethyl-benzyl)-azetidine-3-carboxylic acid has an X-ray powder diffraction pattern that is substantially the same as the X-ray powder diffraction pattern shown in FIG. 3.

15. A method of treating disorders or diseases mediated by lymphocytes, in a subject in need of such treatment, said method comprising administering to said subject a pharmaceutical composition comprising a therapeutically effective amount of a tartrate salt of 1-(4-{1-[(E)-4-cyclohexyl-3-trifluoromethyl-benzyloxyimino]-ethyl}-2-ethyl-benzyl)-azetidine-3-carboxylic acid and a pharmaceutically acceptable adjuvant, diluent or carrier.

16. A method according to claim 15, wherein the tartrate salt of 1-(4-{1-[(E)-4-cyclohexyl-3-trifluoromethyl-benzyloxyimino]-ethyl}-2-ethyl-benzyl)-azetidine-3-carboxylic acid that is administered is Crystalline Form A of said salt, having an X-ray powder diffraction pattern having at least one specific peak at about 2-theta=6.8°, 13.6°, or 17.9°.

17. A method according to claim 16, wherein said Crystalline Form A of the tartrate salt of 1-(4-{1-[(E)-4-cyclohexyl-3-trifluoromethyl-benzyloxyimino]-ethyl}-2-ethyl-benzyl)-azetidine-3-carboxylic acid has an X-ray powder diffraction pattern that is substantially the same as the X-ray powder diffraction pattern shown in FIG. 4.

18. A method of treating organ or tissue transplant rejection, graft versus host disease, autoimmune diseases, allergic diseases, inflammatory diseases or conditions, or muscle diseases in a subject in need of such treatment, the method comprising administering to said subject a pharmaceutical composition comprising a therapeutically effective amount of a tartrate salt of 1-(4-{1-[(E)-4-cyclohexyl-3-trifluoromethyl-benzyloxyimino]-ethyl}-2-ethyl-benzyl)-azetidine-3-carboxylic acid and a pharmaceutically acceptable adjuvant, diluent or carrier.

19. A method according to claim 18, wherein the tartrate salt of 1-(4-{1-[(E)-4-cyclohexyl-3-trifluoromethyl-benzyloxylmino]-ethyl}-2-ethyl-benzyl)-azetidine-3-carboxylic acid that is administered is Crystalline Form A of said salt, having an X-ray powder diffraction pattern having at least one specific peak at about 2-theta=6.8°, 13.6°, or 17.9°.

20. A method according to claim 19, wherein said Crystalline Form A of the tartrate salt of 1-(4-{1-[(E)-4-cyclohexyl-3-trifluoromethyl-benzyloxyimino]-ethyl}-2-ethyl-benzyl)-azetidine-3-carboxylic acid has an X-ray powder diffraction pattern that is substantially the same as the X-ray powder diffraction pattern shown in FIG. 4.

\* \* \* \* \*